(12) United States Patent
Nahon et al.

(10) Patent No.: US 8,398,632 B1
(45) Date of Patent: Mar. 19, 2013

(54) SURGICAL CLAMP HAVING TREATMENT ELEMENTS

(75) Inventors: Daniel Nahon, Ottawa (CA); Sean Carroll, Beaconsfield (CA); Dan Wittenberger, Pierrefonds (CA); Cristian Petre, Laval (CA); Allan Skanes, London (CA); Alan H. Menkis, London (CA); Réal Ste-Marie, Notre-Dame de Ile-perrot (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 2415 days.

(21) Appl. No.: 11/375,231

(22) Filed: Mar. 14, 2006

Related U.S. Application Data

(62) Division of application No. 10/458,745, filed on Jun. 10, 2003, now Pat. No. 7,044,946.

(51) Int. Cl.
*A61B 18/14* (2006.01)
(52) U.S. Cl. ............................................. 606/51; 606/52
(58) Field of Classification Search ............... 606/20–26, 606/50–52
See application file for complete search history.

(56) References Cited

U.S. PATENT DOCUMENTS

| | | | |
|---|---|---|---|
| 4,745,918 A | 5/1988 | Feucht | |
| 4,867,404 A | 9/1989 | Harrington et al. | |
| 4,873,973 A | 10/1989 | Hagen et al. | |
| 5,071,430 A | 12/1991 | de Salis et al. | |
| 5,304,183 A | 4/1994 | Gourlay et al. | |
| 5,443,463 A | 8/1995 | Stern et al. | |
| 5,496,312 A | 3/1996 | Klicek | |
| 5,536,267 A | 7/1996 | Edwards et al. | |
| 5,565,122 A | 10/1996 | Zinnbauer et al. | |
| 5,733,280 A | 3/1998 | Avitall | |
| 5,759,182 A | 6/1998 | Varney et al. | |
| 5,762,069 A | 6/1998 | Kelleher et al. | |
| 5,904,711 A | 5/1999 | Flom et al. | |
| 6,036,706 A * | 3/2000 | Morejohn et al. | 606/158 |
| 6,039,733 A | 3/2000 | Buysse et al. | |
| 6,063,050 A | 5/2000 | Manna et al. | |
| 6,071,303 A | 6/2000 | Laufer | |
| 6,083,223 A | 7/2000 | Baker | |
| 6,139,563 A | 10/2000 | Cosgrove, III et al. | |
| 6,142,994 A * | 11/2000 | Swanson et al. | 606/41 |
| 6,152,920 A | 11/2000 | Thompson et al. | |
| 6,161,543 A * | 12/2000 | Cox et al. | 128/898 |
| 6,174,309 B1 | 1/2001 | Wrublewski et al. | |

(Continued)

FOREIGN PATENT DOCUMENTS

| | | |
|---|---|---|
| CA | 2482416 | 4/1999 |
| CA | 2407645 A1 | 1/2001 |

OTHER PUBLICATIONS

Riemersa, D.J., et al., The Cryo-Jaw, A Clamp Designed for In Vitro Rheology Studies of Horse Digital Flexor Tendons, *J. Biomechanics*, vol. 15, No. 8, pp. 619-620, 1982.

(Continued)

*Primary Examiner* — Michael Peffley
(74) *Attorney, Agent, or Firm* — Christopher & Weisberg, P.A.

(57) ABSTRACT

A medical device is provided having a means for actuating a pair of opposing jaw members. The jaw members are movable relative to one another from a first position, wherein the jaw members are disposed in a spaced apart relation relative to one another, to a second position, wherein the jaw members cooperate to grasp tissue therebetween. An ablation tool is connected to at least one of the jaws members, such that the jaw members are capable of conducting ablation energy through the tissue grasped therebetween.

36 Claims, 10 Drawing Sheets

U.S. PATENT DOCUMENTS

| | | | |
|---|---|---|---|
| 6,179,834 B1 | 1/2001 | Buysse et al. | |
| 6,187,003 B1 | 2/2001 | Buysse et al. | |
| 6,206,877 B1 | 3/2001 | Kese et al. | |
| 6,217,528 B1 | 4/2001 | Koblish et al. | |
| 6,237,605 B1 | 5/2001 | Vaska et al. | |
| 6,241,722 B1 | 6/2001 | Dobak et al. | |
| 6,270,476 B1 | 8/2001 | Santoianni et al. | |
| 6,352,536 B1 | 3/2002 | Buysee et al. | |
| 6,517,536 B2 | 2/2003 | Hooven et al. | |
| 6,527,767 B2 | 3/2003 | Wang et al. | |
| 6,544,274 B2 | 4/2003 | Danitz et al. | |
| 6,546,935 B2 * | 4/2003 | Hooven | 128/898 |
| 6,746,445 B2 | 6/2004 | Abboud et al. | |
| 6,923,806 B2 | 8/2005 | Hooven et al. | |
| 6,926,712 B2 * | 8/2005 | Phan | 606/41 |
| 7,083,620 B2 * | 8/2006 | Jahns et al. | 606/51 |
| 2002/0015996 A1 | 2/2002 | Blumenfeld et al. | |
| 2002/0052602 A1 | 5/2002 | Wang | |
| 2002/0082593 A1 | 6/2002 | Hareyama et al. | |
| 2002/0143346 A1 | 10/2002 | McGuckin, Jr. et al. | |
| 2003/0004507 A1 | 1/2003 | Francischelli et al. | |
| 2003/0018331 A1 | 1/2003 | Dycus et al. | |
| 2003/0024537 A1 | 2/2003 | Cox et al. | |
| 2003/0120268 A1 | 6/2003 | Bertolero et al. | |
| 2004/0068274 A1 * | 4/2004 | Hooven | 606/151 |

OTHER PUBLICATIONS

Patwardhan, A.M., et al., Intraoperative Radiofrequency Microbipolar Coagulation to Replace Incisions of Maze III Procedure for Correcting Atrial Fibrillation in Patients with Rheumatic Valvular Disease, *European Journal of Cario-Thoracic Surgery*, 12 (1997) 627 633.

Sjhattock, M.J., et al., A Cryoclamp for the Rapid Cryofixation of the Isolated Blood-Perfused Rabbit Cardia Papillary Muscle Preparation at Predefined times During the Contraction Cycle, *Journal of Microscopy*, vol. 192, Pt. 3, pp. 269-279, Dec. 1998.

* cited by examiner

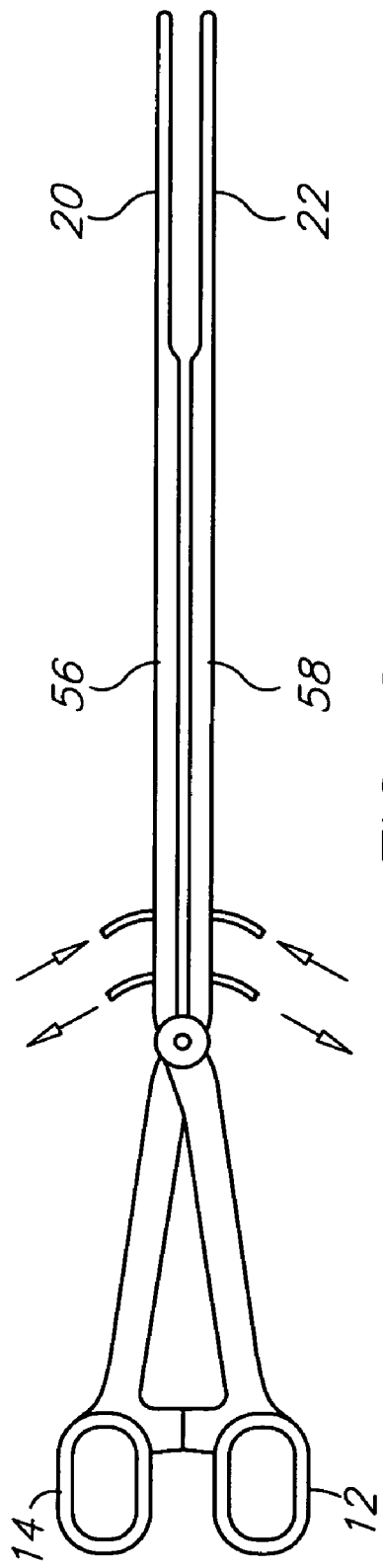
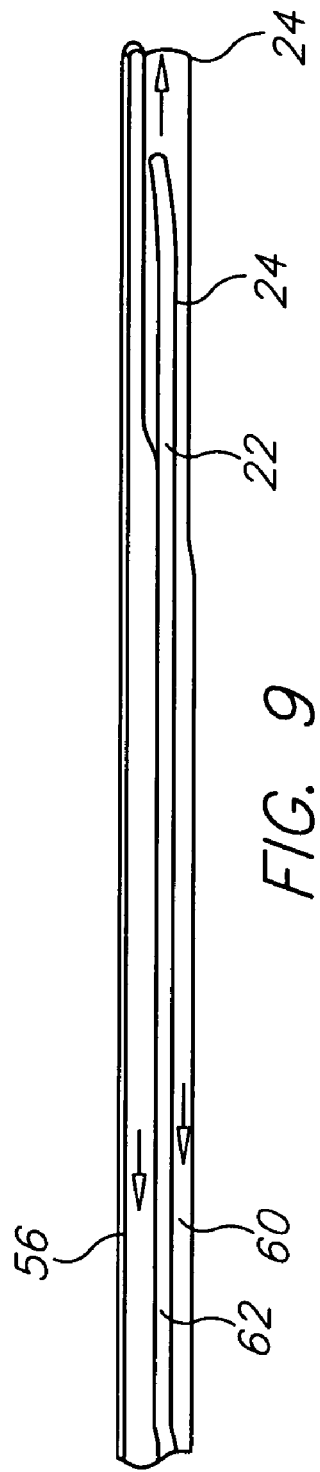
FIG. 8
FIG. 9

SURGICAL CLAMP HAVING TREATMENT ELEMENTS

CROSS-REFERENCE TO RELATED APPLICATION

This application is a divisional of U.S. application Ser. No. 10/458,745 file Jun. 10, 2003 now U.S. Pat. No. 7,044,946, issued May 16, 2006, by Daniel Nahon, et al., entitled SURGICAL CLAMP HAVING TREATMENT ELEMENTS, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for ablating tissue, and more particularly to a medical device having a pair of opposing jaws used for tissue ablation.

BACKGROUND OF THE INVENTION

It is well documented that atrial fibrillation (AF), either alone or as a consequence of other cardiac disease, continues to persist as the most common type of cardiac arrhythmia. In the United States, AF currently affects an estimated two million people, with approximately 160,000 new cases being diagnosed each year. The cost of treatment for AF alone is estimated to be in excess of $400 million worldwide each year.

Although pharmacological treatment is available for AF, the treatment is far from perfect. For example, certain antiarrhythmic drugs, like quinidine and procainamide, can reduce both the incidence and the duration of AF episodes. Yet, these drugs often fail to maintain sinus rhythm in the patient. Cardioactive drugs, like digitalis, Beta blockers, and calcium channel blockers, can also be given to control AF by restoring the heart's natural rhythm and limiting the natural clotting mechanism of the blood. However, antiarrhythmic drug therapy often becomes less effective over time. In addition, antiarrhythmic drug can have severe side effects, including pulmonary fibrosis and impaired liver function.

Another therapy for AF is surgery. In a technique known as the "Maze" procedure, a surgeon makes several incisions through the wall of the atrium with a scalpel and then sews the cuts back together, creating a scar pattern. The scars isolate and contain the chaotic electrical impulses to control and channel the electrical signals. The Maze procedure is expensive, complicated to perform, and associated with long hospital stays and high morbidity.

An alternative to open heart or open chest surgery is a minimally invasive treatment in which ablation devices are used to form scars in various locations in the atrial tissue. Ablation devices that apply heat or cold to body tissue are known. Typically, these devices have an elongate, highly-flexible shaft with a steerable distal end for negotiating a path through the body of a patient. Rigid shaft devices are used in more invasive procedures where a more local opening or direct access to a treatment site is available or created.

It is important to note that these devices are used in an attempt to ablate tissue through the full thickness of the cardiac wall, and thus create a risk associated with damaging structures within or on the outer surface of the cardiac wall. Accordingly ablation devices have been developed which include opposing jaw members to ablate tissue from both sides of the cardiac wall. For example, U.S. Pat. Nos. 6,161,543 to Cox; 5,733,280 to Avitall; and 6,517,536 to Hooven describe techniques for ablating tissue of organs or vessels having opposing walls and disclose ablation devices having clamping members to clamp a treatment site therebetween. Such devices include rigid members/shafts to facilitate reaching the tissue treatment site.

While rigid shafts may be useful in some applications, they have certain limitations as well. For example, without a preset shape for reaching a particular location in the body of a patient, the rigid nature of the shaft limits the area of tissue that can be reached and treated. Even where a relatively large incision is provided, tissue areas that are not at least somewhat directly accessible cannot be reached.

Although a rigid shaft can be provided with a predetermined shape, one must select a device with a rigid shaft that has the most appropriate shape for positioning the working portion of the device in contact with the treatment site in view of the particular anatomical pathway to be followed in the patient. It will be appreciated that a large inventory of devices having rigid shafts may be required to accommodate the various treatment sites and patient anatomies. As an example, U.S. Pat. No. 6,161,543 to Cox el al. describes a variety of rigid probe shapes. Further, for a patient having a relatively uncommon anatomic configuration and/or a difficult to reach treatment site, all rigid devices of an existing set may have less than optimal shapes for positioning. This may impair the prospects of successfully carrying out the treatment procedure. For an ablation device which must bear against tissue at the remote region to create lesions, the contour followed by the device in reaching the target site will in general further restrict the direction and magnitude of the movement and forces which may be applied or exerted on the working portion of the device to effect tissue contact and treatment.

SUMMARY OF THE INVENTION

The present invention advantageously provides a medical device for ablating tissue including a pair of opposing jaws positionable from a first position to a second position. The pair of opposing jaws includes at least one an ablation tool disposed thereon, such that the opposing jaws are capable of conducting ablation energy through the tissue grasped therebetween. A shaft assembly is operably connected to the opposing jaws, wherein the shaft assembly has a malleability such that the shaft assembly retains a first shape until manipulated to a second shape.

A handle assembly is attached to the shaft assembly opposite the opposing jaws. The handle assembly is operably connected to the opposing jaws such that the handle assembly moves the opposing jaws from a first position, wherein the opposing jaws are in a spaced apart relation, to a second position, wherein the opposing jaws grasp the tissue to be treated.

The present invention advantageously provides a method of ablating tissue using the above medical device. The shaft assembly is manipulated from the first shape to the second shape, wherein the second shape is determined by the anatomy of the patient. The opposing jaws are positioned in the first position, such that the opposing jaws are in a spaced apart relation. The medical device is placed about the tissue treatment site, such that the opposing jaws are about the tissue to be treated. The opposing jaws are positioned in the second position, wherein the opposing jaws grasp the tissue to be treated, and the ablation tool is in contact with the tissue treatment site. The tissue is treated by providing ablating energy to the ablating tool.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 8 is a plan view of the surgical clamp of FIG. 1 including elongated shafts;

FIG. 9 is a sectional view of the elongated shaft and ablation segment of the surgical clamp of FIG. 8;

DETAILED DESCRIPTION OF THE INVENTION

The present invention provides a medical device having a handle assembly for actuating a pair of opposing jaw members. The jaw members are movable relative to one another from a first position, wherein the jaw members are disposed in a spaced apart relation relative to one another, to a second position, wherein the jaw members cooperate to grasp tissue therebetween. An ablation tool is connected to at least one of the jaw members, such that the jaw members are capable of conducting ablation energy through the tissue grasped therebetween.

Figure 1:
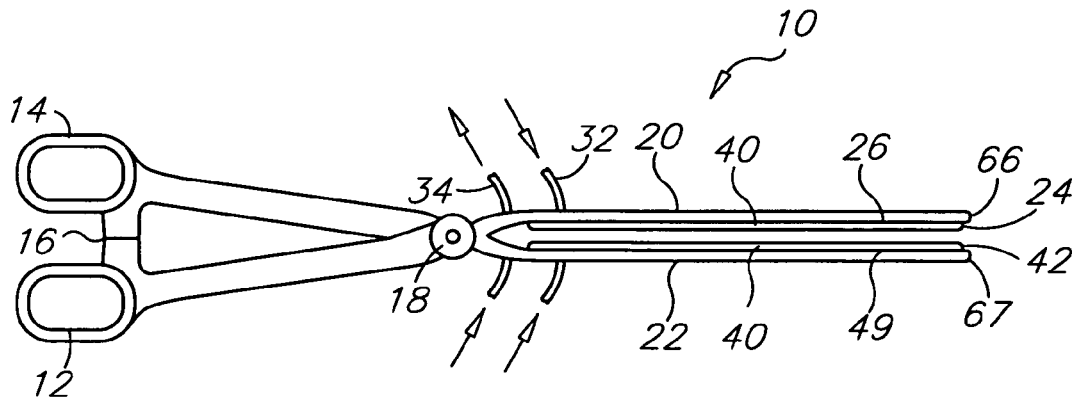
FIG. 1 is a plan view of a surgical clamp in accordance with the present invention.

Referring now to the figures in which like reference designators refer to like elements, there is shown in FIG. 1 a plan view of an exemplary embodiment of the medical device constructed in accordance with the principles of the present invention and designated generally as surgical clamp 10. The surgical clamp 10 includes a handle assembly having elongated handles 12 and 14 and may optionally include a lock mechanism 16, similar to a conventional surgical hemostat. The elongated handles 12, 14 are connected to one another by pivot or hinge 18, and continue distally in the form of a first elongated jaw 20 and a second elongated jaw 22. At least one of the elongated jaws 20, 22 includes an ablation tool. For example, the first elongated jaw 20 includes an ablation tool 24 positioned on the inner surface 26 of the first elongated jaw 20.

Figure 2:
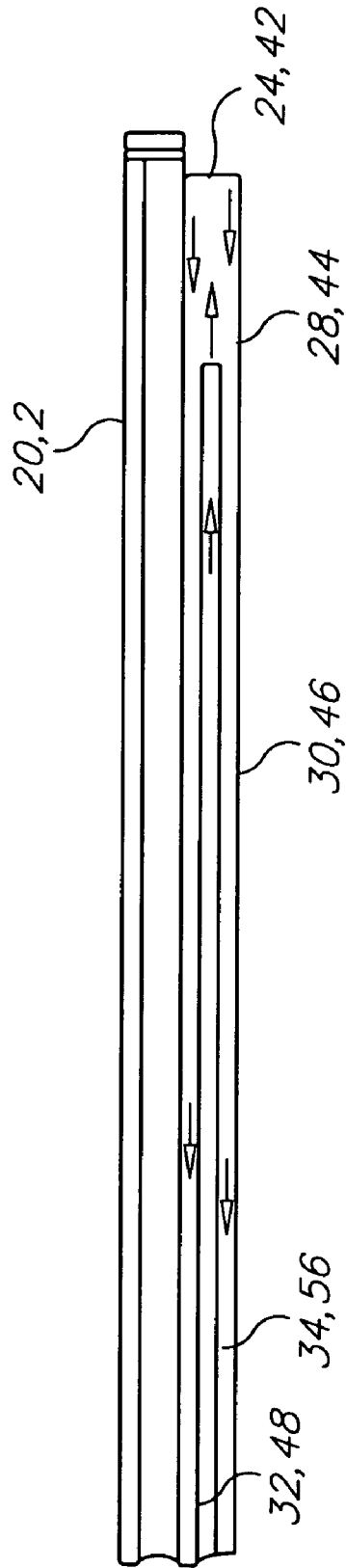
FIG. 2 is a sectional view of an ablation segment of the surgical clamp of FIG. 1.
Figure 3:
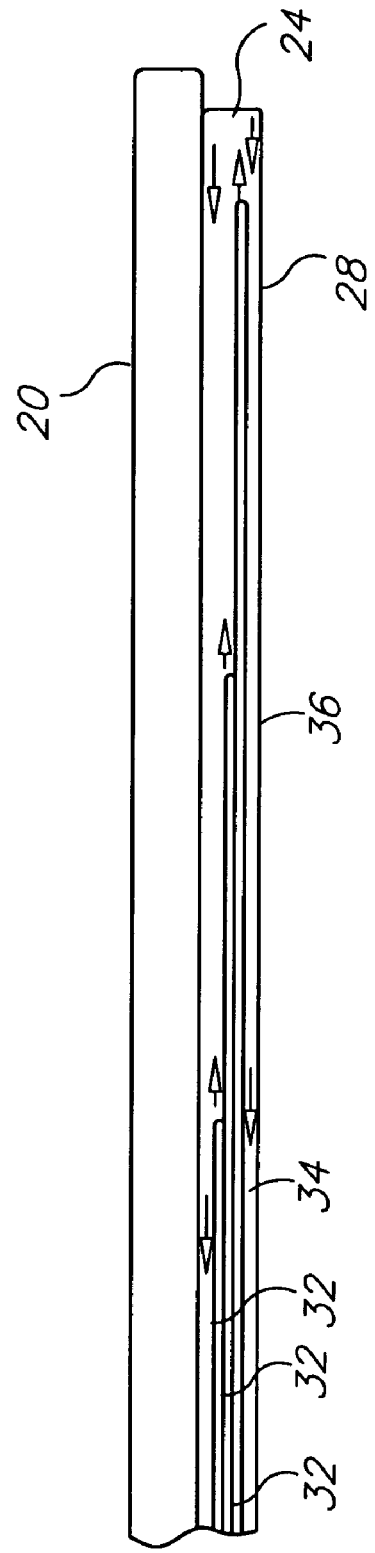
FIG. 3 is a sectional view of an ablation segment including multiple injection tubes of the surgical clamp of FIG. 1.

Referring to FIGS. 2-3, the ablation tool 24 includes an ablation segment 28 having a thermally-transmissive region 30, and defining a fluid path having at least one fluid inlet 32 and a fluid outlet 34 through the ablation tool 24 to the ablation segment 28, wherein the fluid inlet 32 is in fluid communication with a cryogenic fluid source. Also, even though many materials and structures can be thermally conductive or thermally transmissive if chilled to a very low temperature and/or cold soaked, as used herein, a "thermally-transmissive region" is intended to broadly encompass any structure or region of the ablation tool 24 that readily conducts heat.

For example, a metal structure exposed (directly or indirectly) to the cryogenic fluid path is considered a thermally-transmissive region 30 even if an adjacent polymeric or latex portion also permits heat transfer, but to a much lesser extent than the metal. Thus, the thermally-transmissive region 30 can be viewed as a relative term to compare the heat transfer characteristics of different catheter regions or structures, regardless of the material.

Furthermore, while the thermally-transmissive region 30 can include a single, continuous, and uninterrupted surface or structure, it can also include multiple, discrete, thermally-transmissive structures that collectively define a thermally-transmissive region that is elongate or linear. Depending on the ability of the cryogenic system, or portions thereof, to handle given thermal loads, the ablation of an elongate tissue path can be performed in a single or multiple cycle process without having to relocate the catheter one or more times or drag it across tissue.

Figure 4:
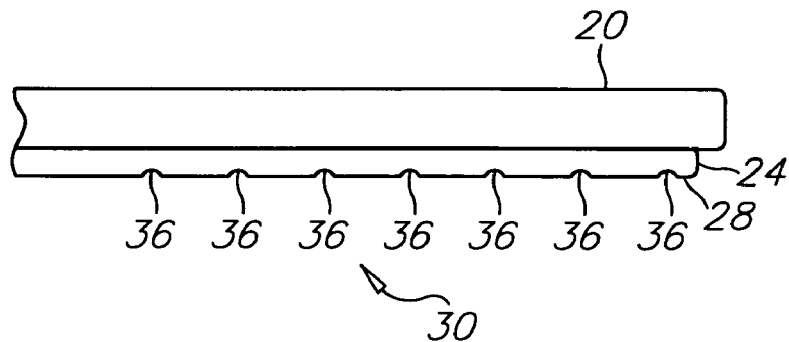
FIG. 4 is a sectional view of an ablation segment including orifices of the surgical clamp of FIG. 1.

In an exemplary embodiment, as shown in FIG. 4, the ablation segment 28 includes one or more orifices 34, where the orifices 34 define the thermally-transmissive region 30. The orifices 34 enable the application of cryogenic fluid directly onto the tissue to be treated.

Additionally, the second elongated jaw 22 can include an ablation tool 42 positioned on the inner surface 44 of the second elongated jaw 22. The ablation tool 42 includes an ablation segment 46 having a thermally-transmissive region 30, and defines a fluid path having at least one fluid inlet 48 and a fluid outlet 50 through the ablation tool 42 to the ablation segment 46, wherein the fluid inlet 48 is in fluid communication with a cryogenic fluid source.

Figure 5:
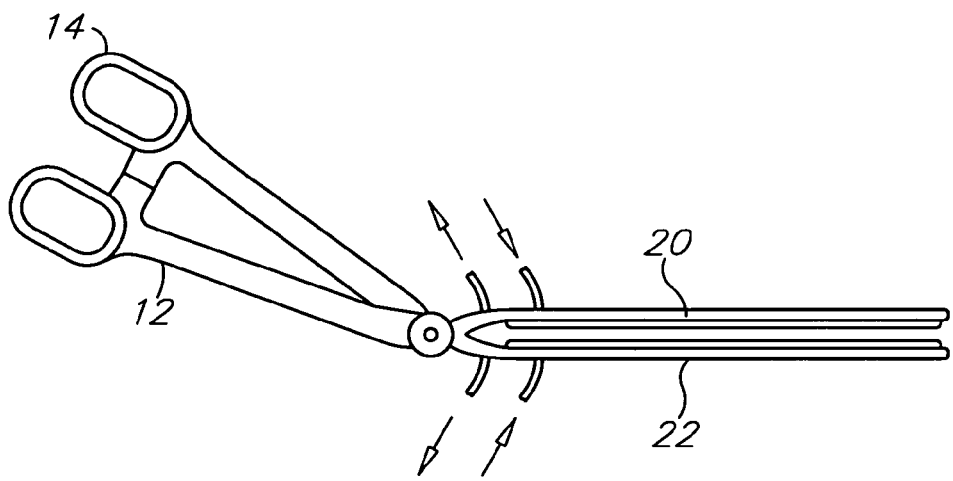
FIG. 5 is a plan view of an alternative embodiment of the surgical clamp of FIG. 1.
Figure 6:
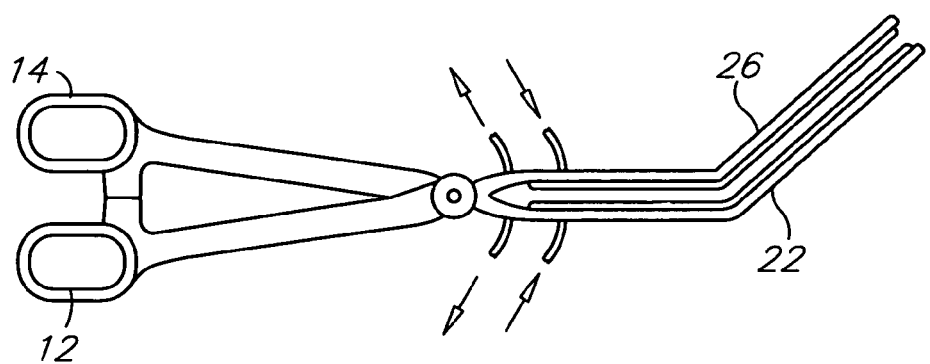
FIG. 6 is a plan view of the surgical clamp of FIG. 1 including curved jaws.

In an exemplary embodiment, as shown in FIG. 5, the handles 12 and 14 are at an acute angle to the first elongated jaw 20 and the second elongated jaw 22. Furthermore, as shown in FIG. 6, the first elongated jaw 20 and the second elongated jaw 22 include a curved portion.

Additionally, the first elongated jaw 20 and the second elongated jaw 22 are malleable, each have a shape-holding deformability, that is, they have rigidity such that the first elongated jaw 20 and the second elongated jaw 22 each retain a first shape until manipulated to a further shape with the application of moderate pressure, and until reshaped. The first elongated jaw 20 and the second elongated jaw 22 retain their shape with sufficient rigidity to manipulate the ablation segment 28 against tissue, and push it past intervening tissue to a desired position.

It is understood that shape, as used herein, is to be construed broadly to include any contour which is needed to configure the first elongated jaw 20 and the second elongated jaw 22 for positioning the active or distal portion of the ablation tool 24, and may include successive bends or segments having more than one curve, angle, deformation or other non-linear configuration. The shape-retaining feature of the first elongated jaw 20 and the second elongated jaw 22 allows an operator to bend the first elongated jaw 20 and the second elongated jaw 22 to a shape or contour, for example around an organ or tissue structure, and have an optimal configuration for positioning and or orienting the active or distal region of the first elongated jaw 20 and the second elongated jaw 22 based upon the particular anatomy of a patient and the location of the treatment site.

Further, the stiffness of first elongated jaw 20 and the second elongated jaw 22 is such that the surgeon can form the first elongated jaw 20 and the second elongated jaw 22 by hand to a desired shape without undue effort, and yet the first elongated jaw 20 and the second elongated jaw 22 retain the set shape as the surgical clamp 10 is maneuvered to and held in position at the treatment site. The first elongated jaw 20 and the second elongated jaw 22 should also be sufficiently rigid such that the surgeon can place the ablation segment 28 of the ablation tool 24 in pressured contact with the tissue treatment site. That is, the first elongated jaw 20 and the second elongated jaw 22 are sufficiently stiff to enable the surgeon to press the ablation segment 28 against the tissue to be treated without inducing a further deformation in the shape of the first elongated jaw 20 and the second elongated jaw 22. The first elongated jaw 20 and the second elongated jaw 22 may in some embodiments deflect slightly, and yet have sufficient stiffness to transfer an effective level of lateral force at their distal end.

In an exemplary embodiment, the first elongated jaw 20 and the second elongated jaw 22 are configured so that they are deformable in a single plane, where the first elongated jaw 20 and the second elongated jaw 22 remain substantially rigid in all other planes. For example, the first elongated jaw 20 and the second elongated jaw 22 can be manipulated in a first plane "P1" from a first shape to a second shape, wherein the first elongated jaw 20 and the second elongated jaw 22 are sufficiently rigid to retain the second shape. The first elongated jaw 20 and the second elongated jaw 22 also have sufficient rigidity such that the first elongated jaw 20 and the second elongated jaw 22 cannot be manipulated in a second plane "P2" orthogonal to the first plane, such that the first elongated jaw 20 and the second elongated jaw 22 are deformable only in the first plane "P1." As such, the first elongated jaw 20 and the second elongated jaw 22 are deformable in only one plane.

Figure 7:
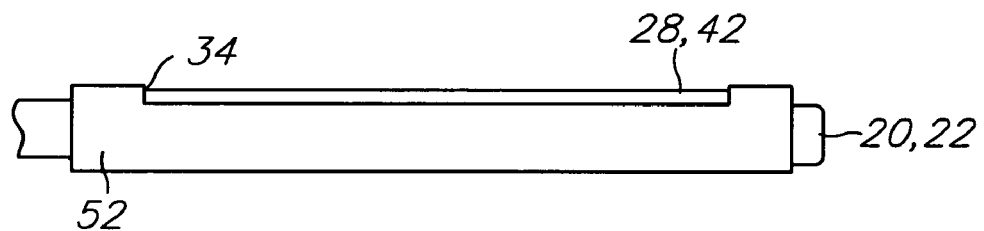
FIG. 7 is a sectional view of an ablation segment including insulation sleeve of the surgical clamp of FIG. 1

In accordance with yet another aspect of the invention, as shown in FIG. 7, particularly directed to the ablative properties of ablation segments 28, 44, the energy distribution during treatment of tissue is further controlled by an adjustable insulation sleeve 52, wherein one each extends over and partially envelops the ablation segments 28, 44. A slotted segment 54 in the insulation sleeve 52 forms a partial circumferential blanket or insulating sleeve which prevents the ablation segments 28,44 from affecting tissue on one side of the ablation segments 28, 44, while leaving the other side of the ablation segments 28, 44 exposed for contact with tissue.

In a further exemplary embodiment, as shown in FIG. 8, the surgical clamp 10 includes a shaft assembly having a first shaft 56 and a second shaft 58 interposed between the handles 12 and 14 and the first elongated jaw 20 and the second elongated jaw 22. The first shaft 56 and a second shaft 58 operably connect the first elongated jaw 20 and the second elongated jaw 22 to the handles 12 and 14 such that the first elongated jaw 20 and the second elongated jaw 22 are movable relative to one another from a first position, wherein the first elongated jaw 22 and the second elongated jaw 20 are disposed in a spaced apart relation relative to one another, to a second position, wherein the first elongated jaw 20 and the second elongated jaw 22 cooperate to grasp tissue therebetween.

Referring to FIG. 9, the first shaft 56 is substantially hollow, defining a first lumen 60 having at least one input lumen 62 positioned therein, wherein the first lumen 60 and the at least one lumen 62 define a fluid path to the ablation tool 24 on the first elongated jaw 20. The first lumen 60 and the at least one lumen 62 are in fluid communication with the ablation fluid outlet 34 and the ablation fluid inlet 32.

Additionally, similar to the first shaft 56, the second shaft 58 can be substantially hollow, defining a first lumen having at least one input lumen positioned therein, wherein the first lumen 60 and the at least one lumen 62 define a fluid path to the ablation tool 42 on the second elongated jaw 22. The first lumen and the at least one lumen 62 are in fluid communication with the ablation fluid outlet 48 and the ablation fluid inlet 50.

The first shaft 56 and the second shaft 58 are malleable, each have a shape-holding deformability, that is, they have a rigidity such that the first shaft 56 and the second shaft 58 each retain a first shape until manipulated to a further shape with the application of moderate pressure, and until reshaped. The first shaft 56 and the second shaft 58 retain their shape with sufficient rigidity to close the first elongated jaw 20 and the second elongated jaw 22 to grasp the tissue, and push it past intervening tissue to a desired position.

It is understood that shape, as used herein, is to be construed broadly to include any contour which is needed to configure the surgical clamp 10 for positioning the active or distal portion of the ablation tool 24, and may include successive bends or segments having more than one curve, angle, deformation or other non-linear configuration. The shape-retaining feature of the first shaft 56 and the second shaft 58 allows an operator to bend the first shaft 56 and the second shaft 58 to a shape or contour, for example around an organ or tissue structure, and have an optimal configuration for positioning and or orienting the active or distal region of the surgical clamp 10 based upon the particular anatomy of a patient and the location of the treatment site.

Further, the stiffness of the first shaft 56 and the second shaft 58 is such that the surgeon can form the first shaft 56 and the second shaft 58 by hand to a desired shape without undue effort, and yet the first shaft 56 and the second shaft 58 retain the set shape as the surgical clamp 10 is maneuvered to and held in position at the treatment site. The first shaft 56 and the second shaft 58 should also be sufficiently rigid such that the surgeon can place the ablation segment 28 of the ablation tool 24 in pressured contact with the tissue treatment site. That is, the first shaft 56 and the second shaft 58 are sufficiently stiff to enable the surgeon to press the ablation segment 28 against the tissue to be treated without inducing a further deformation in the shape of the first shaft 56 and the second shaft 58. The first shaft 56 and the second shaft 58 may in some embodiments deflect slightly, and yet have sufficient stiffness to transfer an effective level of lateral force at their distal end.

In an embodiment, the first shaft 56 and the second shaft 58 are configured so that they are deformable in a single plane, where the first shaft 56 and the second shaft 58 remain substantially rigid in all other planes. For example, the first shaft 56 and the second shaft 58 can be manipulated in a first plane "P1" from a first shape to a second shape, wherein the first shaft 48 and the second shaft 56 are sufficiently rigid to retain the second shape. The first shaft 56 and the second shaft 58 also have sufficient rigidity such that the first shaft 56 and the second shaft 58 cannot be manipulated in a second plane "P2" orthogonal to the first plane, such that the first shaft 56 and the second shaft 58 are deformable only in the first plane "P1." As such the first shaft 56 and the second shaft 58 are deformable in only one plane.

Figure 10:
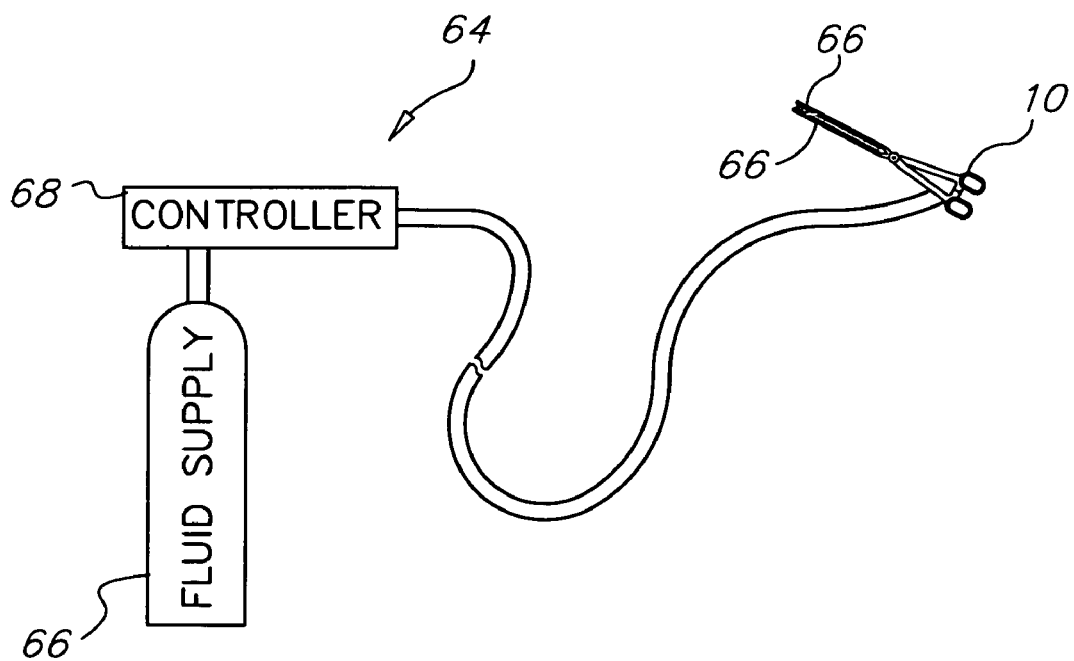
FIG. 10 is a surgical system for operating the surgical clamp in accordance with the present invention.

In an exemplary embodiment, as shown in FIG. 10, the present invention includes an ablation control system 64. The ablation control system 64 includes a supply of cryogenic or cooling fluid 66 in communication with the surgical clamp 10. A fluid controller 68 is interposed or is in-line between the cryogenic fluid supply 66 and the surgical clamp 10 for regulating the flow of cryogenic fluid 66 into the surgical clamp 10 in response to a controller command. Controller commands can include programmed instructions, sensor signals, and manual user input. For example, the fluid controller 68 can be programmed or configured to increase and decrease the pressure of the fluid by predetermined pressure increments over predetermined time intervals.

In another exemplary embodiment, the fluid controller 68 can be responsive to input from a user input device to permit flow of the cryogenic fluid 66 into the surgical clamp 10. As also shown in FIG. 1, one or more temperature sensors 40 in electrical communication with the fluid controller 68 can be provided to regulate or terminate the flow of cryogenic fluid 66 into the surgical clamp 10 when a predetermined temperature at a selected point or points on or within the ablation segment 28 is/are obtained. For example a temperature sensor 40 can be placed at a point proximate the ablation tool 24 distal end and other temperature sensors 40 can be placed at spaced intervals between the ablation tool 24 distal end and another point that is between the distal end and the proximal end.

In another exemplary embodiment, one or more sensors 70, such as a ECG leads, in electrical communication with the controller can be provided to regulate or terminate the flow of cryogenic fluid 66 into the ablation tool 24 depending on the electrical activity in the tissue being treated. For example, the first elongated jaw 20 and second elongated jaw 22 may provide feedback that permits a user to gauge the completeness of the ablation. Specifically, a lesion blocks electrical signals because it is non-conductive scar tissue. The first elongated jaw 20 and second elongated jaw 22 can be used to measure the ability of the lesion to block an electrical signal. Referring to FIG. 1, an electrode 70 is affixed one each to the distal ends of the first elongated jaw 20 and second elongated jaw 22. In an exemplary use, the electrodes 70 are used to verify electrical isolation of the lesion created by the ablation tool 24. For example, the first elongated jaw 20 and the second elongated jaw 22 are opened to position an electrode 70 on each side of the lesion. An electrical signal is transmitted from one electrode, through the lesion, to the opposite electrode. The lesion is considered electrically isolated if the receiving electrode is electrically silent to the signal.

Alternatively, the electrical sensors can be replaced or supplemented with pressure sensors. The pressure sensors can be used to determine when the ablation segment is in physical contact with the tissue to be treated.

The cryogenic fluid can be in a liquid or a gas state, or combination thereof. An extremely low temperature can be achieved within the medical device, and more particularly at the ablation segment by cooling the fluid to a predetermined temperature prior to its introduction into the medical device, by allowing a liquid state cryogenic fluid to boil or vaporize, or by allowing a gas state cryogenic fluid to expand. Exemplary liquids include chlorodifluoromethane, polydimethylsiloxane, ethyl alcohol, HFC's such as AZ-20 (a 50-50 mixture of difluoromethane & pentafluoroethane sold by Allied Signal), and CFC's such as DuPont's Freon. Exemplary gasses include argon, nitrous oxide, and carbon dioxide.

Figure 11:
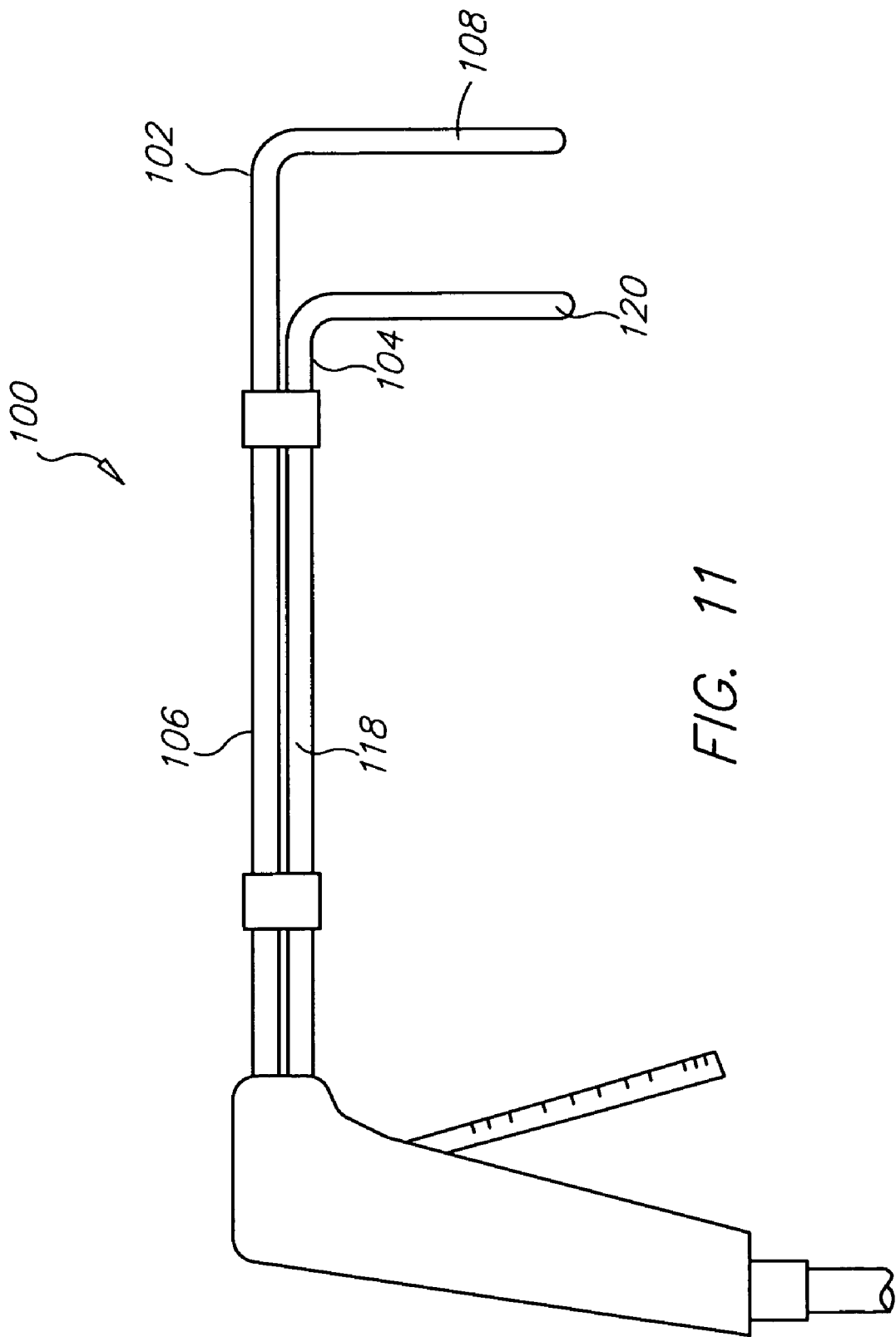
FIG. 11 a plan view of an alternative surgical clamp in accordance with the present invention.

Referring now to FIG. 11, there is shown a plan view of an exemplary embodiment of a medical device constructed in accordance with the principles of the present invention and designated generally as surgical clamp 100. The surgical clamp 100 includes a shaft assembly having opposing jaw assemblies 102, 104 with jaw assembly 102 being fixed and jaw assembly 104 being movable between a first position, wherein the jaw assemblies 102 and 104 are disposed in a spaced apart relation relative to one another, to a second position, wherein the jaw assemblies 102 and 104 cooperate to grasp tissue therebetween.

Figure 12:
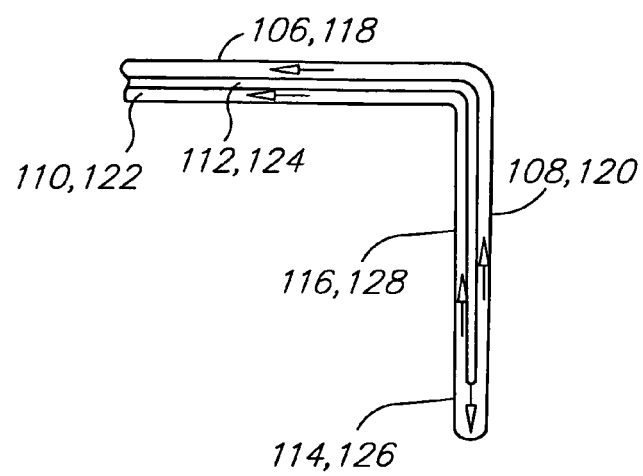
FIG. 12 is a sectional view of an elongated shaft and ablation segment of the surgical clamp of FIG. 11.

The fixed jaw assembly 102 includes a fixed extension shaft 106 and an ablation tool 108 disposed on the distal end of the fixed extension shaft 106, at an acute angle to the fixed extension shaft 106. As shown in FIG. 12, the fixed extension shaft 106 defines a first lumen 110 having at least one input lumen 112 positioned therein, wherein the first lumen 110 and the at least one input lumen 112 define a fluid path to the ablation tool 108, wherein the at least one input lumen 112 is in fluid communication with a cryogenic fluid source. The ablation tool 108 includes an ablation segment 114 with a thermally-transmissive region 116, defines a fluid path through the ablation tool 108 to the ablation segment 112, wherein the fluid path is in fluid communication with the first lumen 110 and the at least one input lumen 112.

The moveable jaw assembly 104 includes a movable extension shaft 118 and a moveable jaw 120 disposed on the distal end of the moveable extension shaft 118 at an acute angle to the moveable extension shaft 118. The moveable extension shaft 118 is operably connected to the fixed extension shaft 106, such that the moveable extension shaft 118 slides along the fixed extension shaft 106 to move the moveable jaw 120 between a first position, wherein the moveable jaw 120 and the ablation tool 108 are disposed in a spaced apart relation relative to one another, to a second position, wherein the moveable jaw 120 and the ablation tool 108 cooperate to grasp tissue therebetween.

In an exemplary embodiment, the ablation tool 108 and the moveable jaw 120 are malleable, each having a shape-holding deformability, that is, they have rigidity such that the ablation tool 108 and the moveable jaw 120 each retain a first shape until manipulated to a further shape with the application of moderate pressure, and until reshaped. The ablation tool 108 and the moveable jaw 120 retain their shape with sufficient rigidity to manipulate the ablation segment 114 against the tissue, and push it past intervening tissue to a desired position.

It is understood that shape, as used herein, is to be construed broadly to include any contour which is needed to configure the ablation tool 108 and the moveable jaw 120 for positioning the active or distal portion of the ablation tool 104, and may include successive bends or segments having more than one curve, angle, deformation or other non-linear configuration. The shape-retaining feature of the ablation tool 108 and the moveable jaw 120 allows an operator to bend the ablation tool 108 and the moveable jaw 120 to a shape or contour, for example around an organ or tissue structure, and have an optimal configuration for positioning and or orienting the active or distal region of the ablation tool 108 and the moveable jaw 120 based upon the particular anatomy of a patient and the location of the treatment site.

Further, the stiffness of the ablation tool 108 and the moveable jaw 120 is such that the surgeon can form the ablation tool 108 and the moveable jaw 120 by hand to a desired shape without undue effort, and yet the ablation tool 108 and the moveable jaw 120 retain the set shape as the surgical clamp 100 is maneuvered to and held in position at the treatment site. The ablation tool 108 and the moveable jaw 120 should also be sufficiently rigid such that the surgeon can place the ablation tool 108 and the moveable jaw 120 in pressured contact with the tissue treatment site. That is, the ablation tool 108 and the moveable jaw 120 are sufficiently stiff to enable the surgeon to press the ablation segment 114 against the tissue to be treated without inducing a further deformation in the shape of the ablation tool 108 and the moveable jaw 120. The ablation tool 108 and the moveable jaw 120 may in some embodiments deflect slightly, and yet has sufficient stiffness to transfer an effective level of lateral force at its distal end.

In an exemplary embodiment, the ablation tool 108 and the moveable jaw 120 are configured so that they are deformable in a single plane, where the ablation tool 108 and the moveable jaw 120 remain substantially rigid in all other planes. For example, the ablation tool 108 and the moveable jaw 120 can be manipulated in a first plane "P1" from a first shape to a second shape, wherein the ablation tool 108 and the moveable jaw 120 are sufficiently rigid to retain the second shape. The ablation tool 108 and the moveable jaw 120 also have sufficient rigidity such that the ablation tool 108 and the moveable jaw 120 cannot be manipulated in a second plane "P2" orthogonal to the first plane, such that the ablation tool 108 and the moveable jaw 120 are deformable only in the first plane "P1." As such the ablation tool 108 and the moveable jaw 120 are deformable in only one plane.

In an exemplary embodiment, the fixed extension shaft 106 and the moveable extension shaft 118 are malleable, each have a shape-holding deformability, that is, they have a rigidity such that the fixed extension shaft 106 and the moveable extension shaft 118 shaft each retain a first shape until manipulated to a further shape with the application of moderate pressure, and until reshaped. The fixed extension shaft 106 and the moveable extension shaft 118 retain their shape with sufficient rigidity to close the ablation tool 108 and the moveable jaw 120 to grasp the tissue, and push it past intervening tissue to a desired position. The shape-retaining feature of the fixed extension shaft 106 and the moveable extension shaft 118 allows an operator to bend the fixed extension shaft 106 and the moveable extension shaft 118 to a shape or contour, for example around an organ or tissue structure, and have an optimal configuration for positioning and or orienting the active or distal region of the surgical clamp 100 based upon the particular anatomy of a patient and the location of the treatment site.

It is understood that shape, as used herein, is to be construed broadly to include any contour which is needed to configure the fixed extension shaft 106 and the moveable extension shaft 118 for positioning the active or distal portion of the ablation tool 104, and may include successive bends or segments having more than one curve, angle, deformation or other non-linear configuration. The shape-retaining feature of the fixed extension shaft 106 and the moveable extension shaft 118 allows an operator to bend the fixed extension shaft 106 and the moveable extension shaft 118 to a shape or contour, for example around an organ or tissue structure, and have an optimal configuration for positioning and or orienting the active or distal region of the fixed extension shaft 106 and the moveable extension shaft 118 based upon the particular anatomy of a patient and the location of the treatment site.

Further, the stiffness of the fixed extension shaft 106 and the moveable extension shaft 118 is such that the surgeon can form the fixed extension shaft 106 and the moveable extension shaft 118 by hand to a desired shape without undue effort, and yet the fixed extension shaft and the moveable extension shaft retains the set shape as the surgical clamp 100 is maneuvered to and held in position at the treatment site. The fixed extension shaft 106 and the moveable extension shaft 118 should also be sufficiently rigid such that the surgeon can place the ablation segment of the ablation segment 114 in pressured contact with the tissue treatment site. That is, the fixed extension shaft 106 and the moveable extension shaft 118 are sufficiently stiff to enable the surgeon to press the ablation segment 114 against the tissue to be treated without inducing a further deformation in the shape of the fixed extension shaft 106 and the moveable extension shaft 118. The fixed extension shaft 106 and the moveable extension shaft 118 may in some embodiments deflect slightly, and yet haves sufficient stiffness to transfer an effective level of lateral force at its distal end.

In an embodiment, the fixed extension shaft 106 and the moveable extension shaft 118 are configured so that they are deformable in a single plane, where the fixed extension shaft 106 and the moveable extension shaft 118 remain substantially rigid in all other planes. For example, the fixed extension shaft 106 and the moveable extension shaft 118 can be manipulated in a first plane "P1" from a first shape to a second shape, wherein the fixed extension shaft 106 and the moveable extension shaft 118 are sufficiently rigid to retain the second shape. The fixed extension shaft 106 and the moveable extension shaft 118 also have sufficient rigidity such that the fixed extension shaft 106 and the moveable extension shaft 118 cannot be manipulated in a second plane "P2" orthogonal to the first plane, such that the fixed extension shaft 106 and the moveable extension shaft 118 are deformable only in the first plane "P1." As such the fixed extension shaft 106 and the moveable extension shaft 118 are deformable in only one plane.

Referring to FIG. 12, the moveable extension shaft 118 defines a first lumen 122 having at least one input lumen 124 positioned therein, the first lumen 122 and the at least one input lumen 124 defining a fluid path to the moveable jaw 120, wherein the at least one fluid input lumen 124 is in fluid communication with a cryogenic fluid source. The moveable jaw 120 is an ablation tool including an ablation segment 126 with a thermally-transmissive region 128, and defining a fluid path through the moveable jaw 120 to the ablation segment 126, wherein the fluid path is in fluid communication with the first lumen 122 and the at least one input lumen 124.

The fixed jaw assembly 102 and the moveable jaw 104 assembly are operably connected to a handle assembly 103. The handle assembly 130 includes a fixed handle 132 attached to the fixed extension shaft 106 and a lever arm 134 pivotally connected to the fixed handle 132. The lever arm 134 is attached to the movable extension shaft, 118 such that as the lever arm 134 pivots about the fixed handle 132 from a start position, the moveable jaw 120 moves from a first position to a second position.

Figure 13:
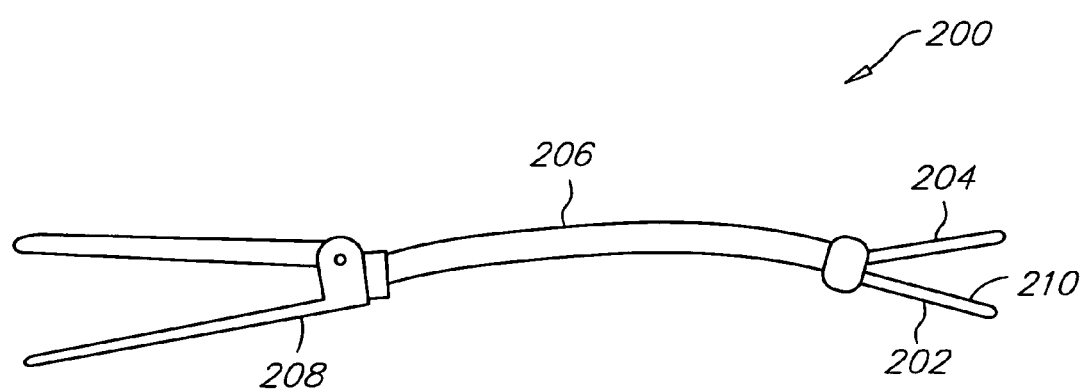
FIGS. 13-17 illustrate additional configurations of a surgical clamp.

Referring now to FIG. 13, there is shown a plan view of an exemplary embodiment of a medical device constructed in accordance with the principles of the present invention and designated generally as surgical clamp 200. The surgical clamp 200 includes a jaw assembly having a first jaw 202, and a second jaw 204 in opposing relation. The first jaw 202 and the second jaw 204 are movable between a first position, wherein the first jaw 202 and the second jaw 204 are disposed in a spaced apart relation relative to one another, to a second position, wherein the first jaw 202 and the second jaw 204 cooperate to grasp tissue therebetween. The first jaw 202 and the second jaw 204 are connected to an elongated shaft assembly 206, wherein a handle assembly 208 is connected to the elongated shaft assembly 206 opposite the first jaw 202 and the second jaw 204. At least one of the first jaw 202 and the second jaw 204 includes an ablation tool. For example, the first jaw 202 includes an ablation tool 210 positioned on the inner surface 212 of the first jaw 202.

The elongated shaft assembly 206 defines a first lumen 212 having at least one input lumen 214 positioned therein. The first lumen 212 and the at least one input lumen 214 define a fluid path to the ablation tool 210, wherein the at least one input lumen 214 is in fluid communication with a cryogenic fluid source. The ablation tool 201 includes an ablation segment 216 with a thermally-transmissive region 218, and defines a fluid path through the ablation tool to the ablation segment 218, wherein the fluid path is in fluid communication with the first lumen 212 and the at least one input lumen 214.

Additionally, the second jaw 204 can include an ablation tool 220 having an ablation segment 222 with a thermally-transmissive region 224, and defining a fluid path through the ablation tool 220 to the ablation segment 222, wherein the fluid path is in fluid communication with the first lumen 212 and the at least one input lumen 214.

In an exemplary embodiment, the first jaw 202 and the second jaw 204 are malleable, each have a shape-holding deformability, that is, they have rigidity such that the first jaw 202 and the second jaw 204 each retain a first shape until manipulated to a further shape with the application of moderate pressure, and until reshaped. The first jaw 202 and the second jaw 204 retain their shape with sufficient rigidity to manipulate the ablation segment 216 against tissue, and push it past intervening tissue to a desired position.

It is understood that shape, as used herein, is to be construed broadly to include any contour which is needed to configure the first jaw 202 and the second jaw 204 for positioning the active or distal portion of the ablation tool, and may include successive bends or segments having more than one curve, angle, deformation or other non-linear configuration. The shape-retaining feature of the first jaw 202 and the second jaw 204 allows an operator to bend the first jaw 202 and the second jaw 204 to a shape or contour, for example around an organ or tissue structure, and have an optimal configuration for positioning and or orienting the active or distal region of the first jaw 202 and the second jaw 204 based upon the particular anatomy of a patient and the location of the treatment site.

Further, the stiffness of the first jaw 202 and the second jaw 204 is such that the surgeon can form the first jaw 202 and the second jaw 204 by hand to a desired shape without undue effort, and yet the first jaw 202 and the second jaw 204 retain the set shape as the surgical clamp 200 is maneuvered to and held in position at the treatment site. The first jaw 202 and the second jaw 204 should also be sufficiently rigid such that the surgeon can place the ablation segment of the ablation tool in pressured contact with the tissue treatment site. That is, the first jaw 202 and the second jaw 204 are sufficiently stiff to enable the surgeon to press the ablation segment against the tissue to be treated without inducing a further deformation in the shape of the first jaw 202 and the second jaw 204. The first jaw 202 and the second jaw 204 may in some embodiments deflect slightly, and yet have sufficient stiffness to transfer an effective level of lateral force at its distal end.

In an exemplary embodiment, the first jaw 202 and the second jaw 204 are configured so that they are deformable in a single plane, where the first jaw 202 and the second jaw 204 remain substantially rigid in all other planes. For example, the first jaw 202 and the second jaw 204 can be manipulated in a first plane "P1" from a first shape to a second shape, wherein the first jaw 202 and the second jaw 204 are sufficiently rigid to retain the second shape. The first jaw 202 and the second jaw 204 also have sufficient rigidity such that the f first jaw 202 and the second jaw 204 cannot be manipulated in a second plane "P2" orthogonal to the first plane, such that the first jaw 202 and the second jaw 204 are deformable only in the first plane "P1." As such the first jaw 202 and the second jaw 204 are deformable in only one plane.

In an exemplary embodiment, the elongated shaft assembly 206 is malleable, having a shape-holding deformability, that is, it has rigidity such that the elongated shaft assembly 206 retains a first shape until manipulated to a further shape with the application of moderate pressure, and until reshaped. The elongated shaft assembly 206 retains its shape with sufficient rigidity to close the first jaw 202 and the second jaw 204 to grasp the tissue, and push it past intervening tissue to a desired position.

It is understood that shape, as used herein, is to be construed broadly to include any contour which is needed to configure the surgical clamp 200 for positioning the active or distal portion of the ablation tool, and may include successive bends or segments having more than one curve, angle, deformation or other non-linear configuration. The shape-retaining feature of the elongated shaft assembly 206 allows an operator to bend the elongated shaft assembly 206 to a shape or contour, for example around an organ or tissue structure, and have an optimal configuration for positioning and or orienting the active or distal region of the surgical clamp 200 based upon the particular anatomy of a patient and the location of the treatment site.

Further, the stiffness of the elongated shaft assembly 206 is such that the surgeon can form the elongated shaft assembly 206 by hand to a desired shape without undue effort, and yet the elongated shaft assembly 206 retains the set shape as the surgical clamp 200 is maneuvered to and held in position at the treatment site. The elongated shaft assembly 206 should also be sufficiently rigid such that the surgeon can place the ablation segment of the ablation tool in pressured contact with the tissue treatment site. That is, the elongated shaft assembly 206 is sufficiently stiff to enable the surgeon to press the ablation segment against the tissue to be treated without inducing a further deformation in the shape of the elongated shaft assembly 206. The elongated shaft assembly 206 may in some embodiments deflect slightly, and yet has sufficient stiffness to transfer an effective level of lateral force at its distal end.

In an embodiment, the elongated shaft assembly 206 is configured so that it is deformable in a single plane, where the elongated shaft assembly 206 remains substantially rigid in all other planes. For example, the elongated shaft assembly 206 can be manipulated in a first plane "P1" from a first shape to a second shape, wherein the elongated shaft assembly 206 is sufficiently rigid to retain the second shape. The elongated shaft assembly 206 also has sufficient rigidity such that the elongated shaft assembly 206 cannot be manipulated in a second plane "P2" orthogonal to the first plane, such that the elongated shaft assembly 206 is deformable only in the first plane "P1." As such the elongated shaft assembly 206 are deformable in only one plane.

Figure 14:
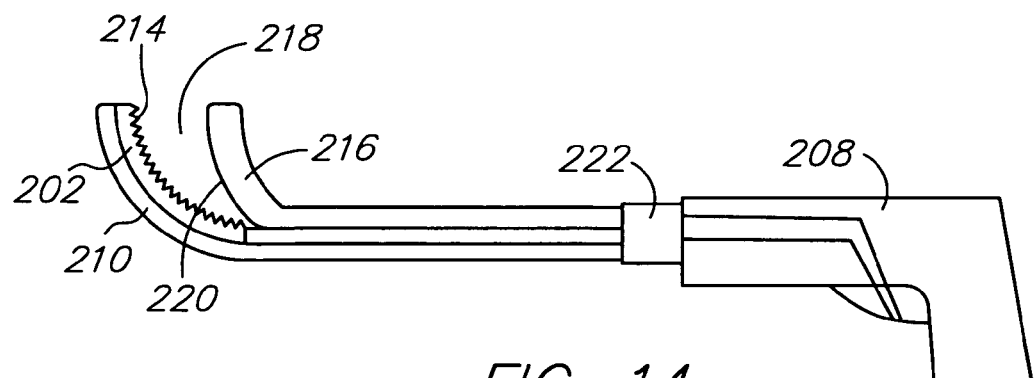

Referring now to FIG. 14, an exemplary tool is shown having a handle portion 208 from which extends a probe 210 having a cooling segment 212. As will all disclosed embodiments, the cooing segment 212 can be provided with a smooth or textured tissue engaging surface 214. In FIG. 14, the tissue-engaging surface 214 is textures to have "teeth." A second element 216 is movable relative to the probe to define a tissue capture zone 218. A distal region 220 of the second element 216 can have a complementary shape to the cooling segment 212 and be smooth (as shown) or textured. As the probe 210 and the second element 216 are moved axially with respect to each other, the tissue capture zone 218 increases or decreases in size. In the illustrated embodiment, the second element 216 is secured to the probe 210 and is axially slidable with respect thereto by axially moving a proximal portion 222 of the second element.

Figure 15:
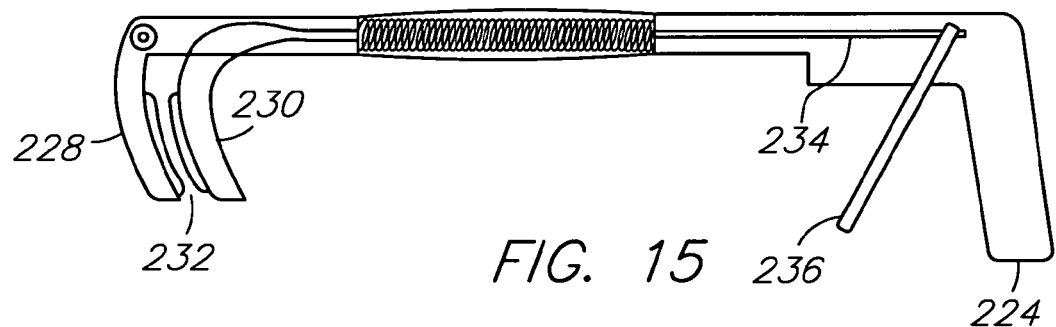

With respect to FIG. 15, a different actuating mechanism is shown in an exemplary tool having a handle portion 224 from which extends a probe 226 having a cooling segment 228. A second element 230 is movable relative to the probe 226 to define a tissue capture zone 232. As the probe 226 and the second element 230 are moved axially with respect to each other, the tissue capture zone 232 increases or decreases in size. In the illustrated embodiment, the second element 230 is secured to the probe 226 and is axially slidable with respect thereto by axially moving a proximal portion 234 of the second element by pulling a handle, lever, or trigger 236 that is engaged with the proximal portion of the second element. A spring 238 or other bias means can be provided to either urge the second element 230 in either the distal or proximal direction.

Figure 16:
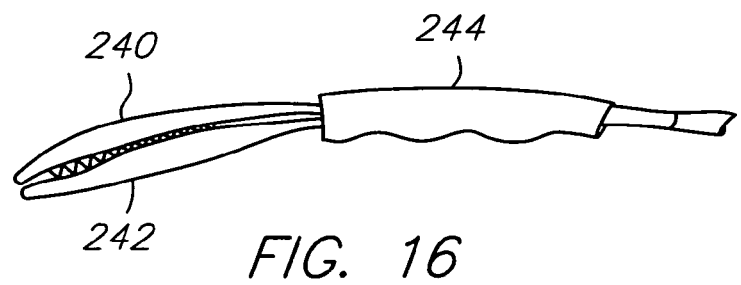

FIG. 16 shows yet another configuration wherein a cooling element 240 is juxtaposed a second element 242 and wherein the elements are biased apart. A sleeve or handle element is slidable with respect to the elements so that as it is moved distally it urges the elements together.

Figure 17:
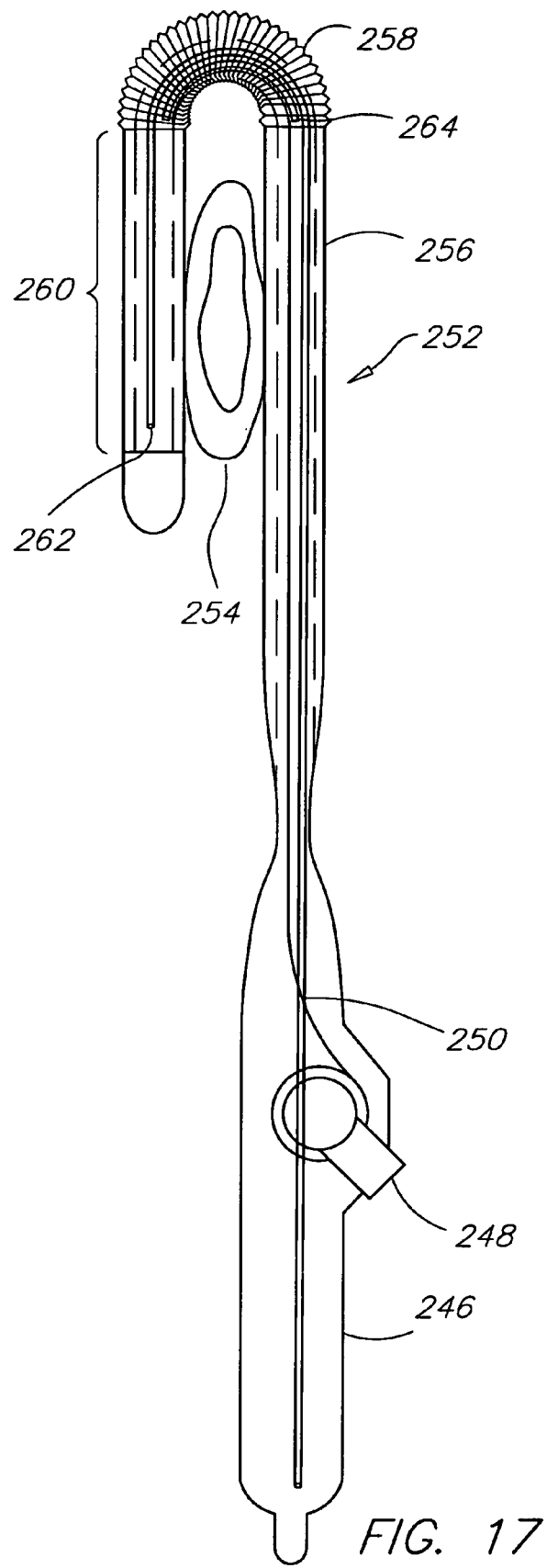

Referring to FIG. 17 another clamping tool is disclosed that includes a handle portion 246 having an actuator 248 that pivots or rotates fore and aft. The actuator 248 is coupled to a pull or push wire 250 that is secured to a distal portion of an elongate shaft structure 252 to cause the shaft structure to clamp tissue 254. As shown, the shaft structure 252 includes an insulating distal portion 256, a bellows or coil portion 258 that provides a clamping effect, and a cooling segment 260. A coolant injection tube 262 introduces coolant into the cooling segment 260. The elongate shaft structure 252 can be transitioned from a substantially linear configuration to the configuration shown or it can be preformed to substantially the configuration shown and actuated to tighten the space between the insulating distal portion 256 and the cooling segment 260 which can further be insulated on its outward face. As shown, the wire 250 is secured at its distal end to a shim 264.

Figure 18:
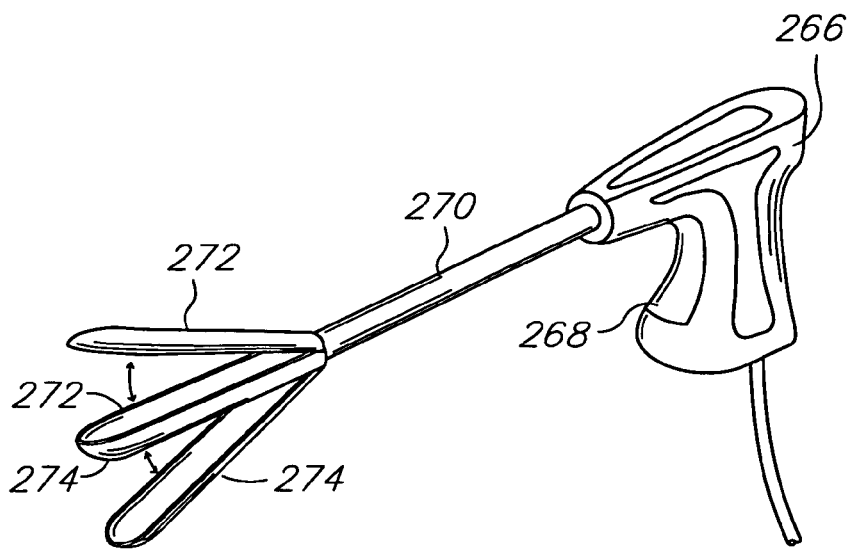
FIG. 18 illustrates still another surgical clamp configuration.

FIG. 18 illustrates yet another configuration of a tool including a handle 266, actuator 268, insulated shaft 270, first jaw 272, and second jaw 274, wherein manipulation of the actuator 268 causes the jaws to open and close or move relative to each other. The figure depicts the jaws in both the open and clamped state. Coolant can flow to and/or through one or both jaws and both jaws can be insulated except at the point where they meet. One or both jaws can be provided with temperature and/or impedance measurement devices to monitor and evaluate lesion formation and characteristics. In an embodiment a temperature sensor is associated with a jaw that does not have a cooling element. The jaws are clamped together with tissue therebetween. The transmurality of a lesion could be ascertained when the temperature sensor detects a temperature of −40 degrees Centigrade for two minutes. Of course time and temperature may be different for different types, conditions and thickness of tissue.

Figure 19:
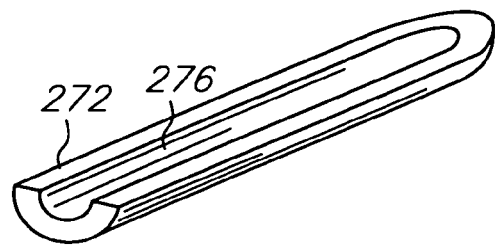
FIGS. 19 and 20 illustrate additional details of the jaw elements shown in FIG. 18.
Figure 20:
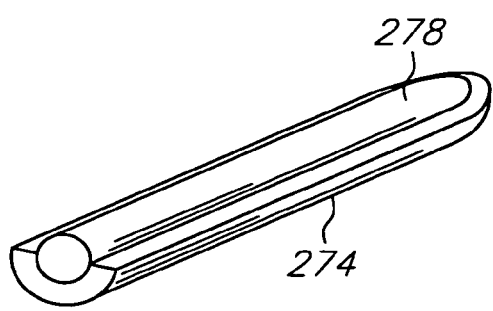

FIGS. 19 and 20 show additional details of the first jaw 272 and the second jaw 274, respectively; wherein the first jaw made of an insulating material defines a recess 276 shaped to receive an elongate cooling element 278 affixed to insulating material.

Although the device of FIG. 18 may include two jaws, one jaw can be removable so that a single jaw with a cooling segment is provided. Thus, the device can be convertible from a clamping tool to a "wand" type device for use in procedures not requiring clamping.

Figure 21:
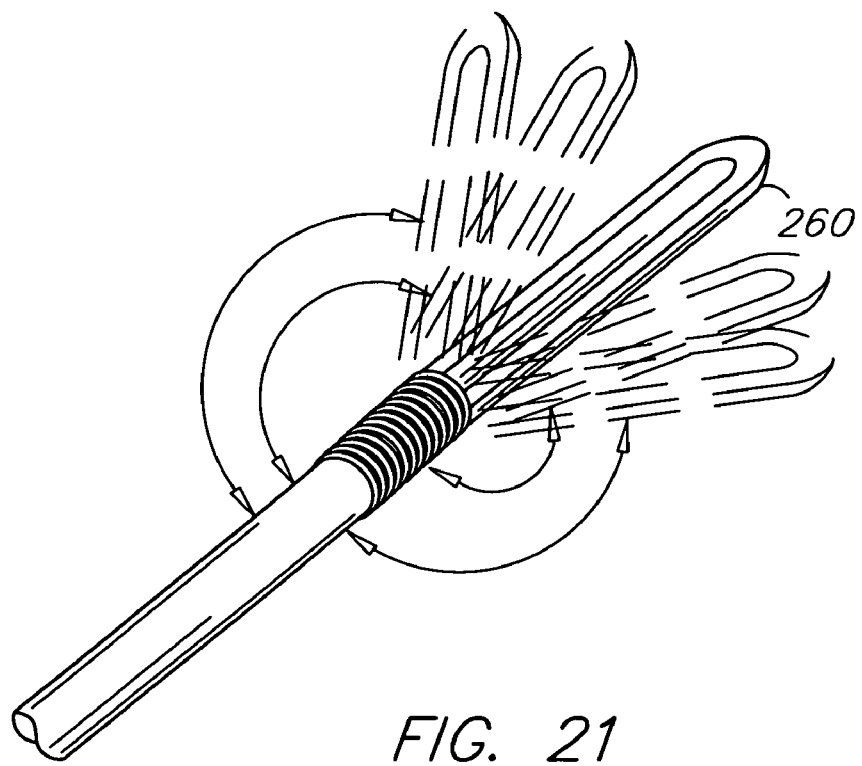
FIGS. 21 and 22 show additional clamp configurations.

FIG. 21 illustrates yet another configuration for the clamping device. Here, cooling segment 260 can be deflected from its normal position to a variety of deflection positions via use of actuator 248 (not shown). Cooling segment 260 may be deflected to an angle of choice my manipulation of the actuator. Coolant can then be introduced to cooling segment 260 via the internal injection tube (not shown).

Figure 22:
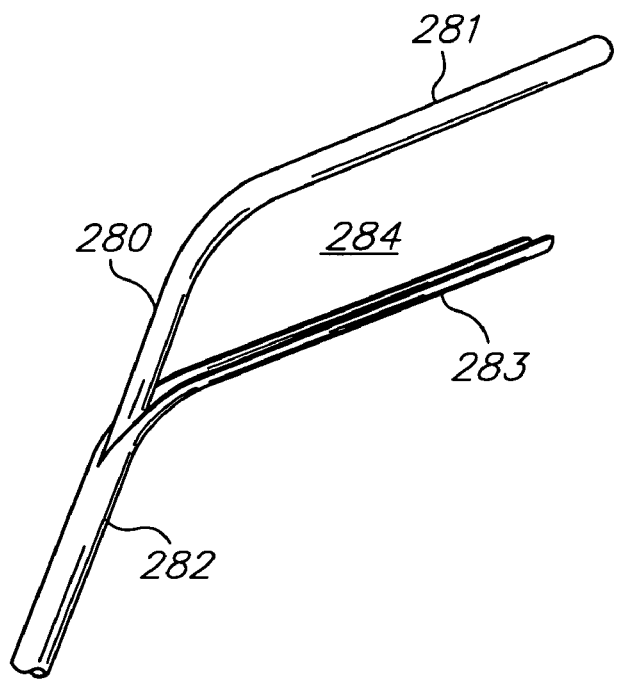

FIG. 22 illustrated yet another configuration for a clamping device wherein a cooling element 280 is slidably disposed within an insulating sheath 282. The distal portion of the cooling element 281 and the distal portion of the sheath 283 are angled with respect to their proximal portion so that extension and retraction of the cooling element with respect to the sheath opens and closes a tissue-clamping zone 284.

Although generally shown as a cryogenic ablation tool, it is understood that in other embodiments the ablation segment applies other types of energy or combination of energies, to the tissue to be treated, including, but not limited to, cryogenic energy, radio frequency (RF) energy, microwave energy, ultrasound energy, laser energy, and contact heating energy. It is further understood that other devices can be coupled to the guide distal end, for example, cameras, video devices, probes and other components can be affixed to the guide for various applications For example, pacing/sensing electrodes can be affixed to points on ton the slotted segment.

The medical device of the present invention is well suited for treating tissue in a variety of locations in the body during invasive surgical procedures. Illustrative applications include open thoracic and peritoneal surgery as well as endoscopic procedures, e.g., treating tissue located at or near the heart, intestines, uterus, and other regions for which surgical or endoscope assisted surgical access and topical tissue treatment, or cauterization or ablation is appropriate, as well as ophthalmic surgery, and tumor ablation and various applications preparatory to further surgical steps.

It will be appreciated by persons skilled in the art that the present invention is not limited to what has been particularly shown and described hereinabove. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device for ablating tissue comprising:
a pair of opposing jaws positionable from a first position to a second position, at least one of the opposing jaws including an ablation element, wherein the pair of opposing jaws are malleable within a first plane and are substantially rigid within a second plane orthogonal to the first plane; and
a shaft assembly operably connected to the opposing jaws, the shaft assembly having a malleability such that the shaft assembly retains a first shape until manipulated to a second shape; the shaft assembly is malleable within a first plane and is substantially rigid within a second plane orthogonal to the first plane.

2. The medical device according to claim 1, further comprising a handle assembly attached to the shaft assembly opposite the pair of opposing jaws, the handle assembly being operably connected to the pair of opposing jaws to move the pair of opposing jaws from the first position to the second position.

3. The medical device according to claim 1, further comprising an ablation control system operably connected to the at least one ablation element.

4. The medical device according to claim 3, further including at least one temperature sensor positioned on at least one of the opposing jaws and operably connected to the ablation control system.

5. The medical device according to claim 3, further including at least one signal electrode positioned on each of the opposing jaws and operably connected to the ablation control system.

6. The medical device according to claim 1, further comprising a moveable insulation sleeve configured to partially surround the at least one ablation element.

7. The medical device according to claim 1, wherein the pair of opposing jaws have a malleability such that the pair of opposing jaws retain a first shape until manipulated to a second shape.

8. The medical device according to claim 1, wherein the at least one ablation tool is configured to circulate cryogenic fluid therethrough for ablation of the tissue contacting the ablation element.

9. The medical device according to claim 8, wherein the at least one ablation element includes at least one orifice such that cryogenic fluid can be applied directly to the tissue.

10. The medical device according to claim 1, wherein the pair of opposing jaws comprise a first jaw and a second jaw, the first jaw including a first jaw ablation tool having at least one first jaw ablation segment.

11. The medical device according to claim 10, wherein the second jaw includes a second jaw ablation tool having at least one second jaw ablation segment.

12. The medical device according to claim 10, wherein the second jaws is removably attached to the shaft.

13. The medical device according to claim 10, wherein the shaft assembly comprises a first shaft attached to the first jaw and a second shaft attached to the second jaw.

14. The medical device according to claim 13, wherein the first shaft and the second shaft are pivotally connected.

15. The medical device according to claim 13, wherein the first shaft and the second shaft are sliding connected.

16. The medical device according to claim 1, wherein the at least one ablation tool is configured to transfer ablation energy selected from the group consisting of cryogenic energy, radio frequency energy, microwave energy, ultrasound energy, laser energy, chemical energy, and contact heating energy.

17. A medical device for ablating tissue comprising:
a first jaw and a second jaw, the first jaw including a first jaw ablation tool having at least one first jaw ablation segment;
a shaft assembly operably connected to the first jaw and the second jaw, the shaft assembly having a malleability such that the shaft assembly retains a first shape until manipulated to a second shape, and the shaft assembly is malleable within a first plane and is substantially rigid within a second plane orthogonal to the first plane; and
a handle assembly attached to the shaft assembly opposite the first jaw and the second jaw, the handle assembly operably connected to the first jaw and the second jaw to move the first jaw and the second jaw from a first position to a second position.

18. The medical device according to claim 17, wherein the second jaw includes a second jaw ablation tool having at least one second jaw ablation segment.

19. The medical device according to claim 18, wherein the second ablation tool is configured to circulate cryogenic fluid there through for ablation of the tissue contacting the second ablation tool.

20. The medical device according to claim 17, wherein the second jaws is removably attached to the shaft.

21. The medical device according to claim 17, wherein the shaft assembly comprises a first shaft attached to the first jaw and a second shaft attached to the second jaw.

22. The medical device according to claim 21, wherein the first shaft and the second shaft are pivotally connected.

23. The medical device according to claim 21, wherein the first shaft and the second shaft are sliding connected.

24. The medical device according to claim 17, further including at least one temperature sensor positioned on the first jaw.

25. The medical device according to claim 17, further including at least one signal electrode positioned on the first jaw and the second jaw.

26. The medical device according to claim 17, wherein the first ablation tool is configured to circulate cryogenic fluid therethrough for ablation of the tissue contacting the ablation tool.

27. The medical device according to claim 17, wherein the first jaw and the second jaws have a malleability such that the first jaw and the second jaw retain a first shape until manipulated to a second shape.

28. The medical instrument according to claim 27, wherein the first jaw and the second jaw are malleable within a first plane and are substantially rigid within a second plane orthogonal to the first plane.

29. A medical device for ablating tissue comprising:
a first jaw and a second jaw, the first jaw including a first jaw ablation tool configured to circulate cryogenic fluid there through and having at least one first jaw ablation segment;
a shaft assembly operably connected to the first jaw and the second jaw, the shaft assembly having a malleability such that the shaft assembly retains a first shape until manipulated to a second shape, and the shaft assembly is malleable within a first plane and is substantially rigid within a second plane orthogonal to the first plane;
a handle assembly attached to the shaft assembly opposite the first jaw and the second jaw, the handle assembly operably connected to the first jaw and the second jaw to move the first jaw and the second jaw from a first position to a second position; and
an ablation control system operably connected to the first ablation tool.

30. The medical device according to claim 29, wherein the second jaw includes a second jaw ablation tool configured to circulate cryogenic fluid there through and having at least one second jaw ablation segment, the second ablation tool being operably connected to the ablation control system.

31. The medical device according to claim 30, wherein the second jaw is removably attached to the shaft.

32. The medical device according to claim 29, wherein the shaft assembly comprises a first shaft attached to the first jaw and a second shaft attached to the second jaw.

33. The medical device according to claim 32, wherein the first shaft and the second shaft are pivotally connected.

34. The medical device according to claim 32, wherein the first shaft and the second shaft are sliding connected.

35. The medical device according to claim 29, further including at least one signal electrode positioned on the first jaw and the second jaw.

36. A method of ablating tissue; comprising:
providing an ablating device having a pair of opposing jaws positionable from a first position to a second position, at least one of said opposing jaws includes an ablation tool, and a shaft assembly operably connected to the opposing jaws, the shaft assembly having a malleability such that the shaft assembly retains a first shape until manipulated to a second shape, the shaft assembly is malleable within a first plane and is substantially rigid within a second plane orthogonal to the first plane;

manipulating the shaft assembly from the first shape to the second shape;

positioning the opposing jaws in the first position such that the opposing jaws are in a spaced apart relation;

placing the opposing jaws about the tissue to be treated;

positioning the opposing jaws in the second position such that the opposing jaws grasp the tissue to be treated; and ablating the tissue to be treated.

* * * * *